United States Patent [19]

Weissman

[11] Patent Number: 4,801,264

[45] Date of Patent: Jan. 31, 1989

[54] DENTAL PIN AND BUSHING ASSEMBLY

[75] Inventor: Bernard Weissman, New York, N.Y.

[73] Assignee: IPCO Corporation, White Plains, N.Y.

[21] Appl. No.: 76,640

[22] Filed: Jul. 23, 1987

[51] Int. Cl.[4] ............................................. A61C 13/00
[52] U.S. Cl. ...................................................... 433/74
[58] Field of Search ................................. 433/74, 221

[56] References Cited

U.S. PATENT DOCUMENTS 3,470,614  10/1969  Kelly ...................................... 433/74

OTHER PUBLICATIONS

Whaledent, Inc., 304 Ashland Place, Brooklyn, New York 11217, "Pin-Mates", Oct. 1968.

Primary Examiner—Robert Peshock
Attorney, Agent, or Firm—Helfgott & Karas

[57] ABSTRACT

A dental pin and bushing assembly for coupling of a removable die portion of a tooth from a working cast. The pin includes an axially extending head portion which can be secured within the die. The coaxial body portion depends from the die portion and includes an offset section for oriented insertion of the pin in the bushing. The bushing is secured in the working cast and includes an elongated sleeve with a mating chamber for receiving the pin. The bushing matingly receives the body portion of the pin so that the removable die can be inserted in only a single oriented direction into the bushing.

21 Claims, 3 Drawing Sheets

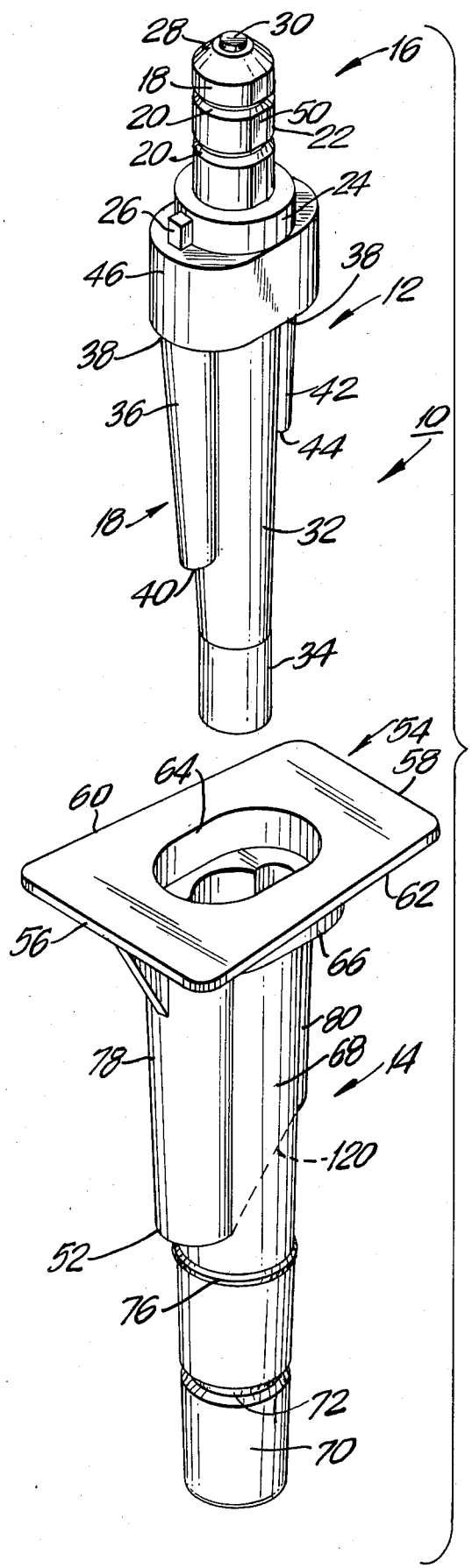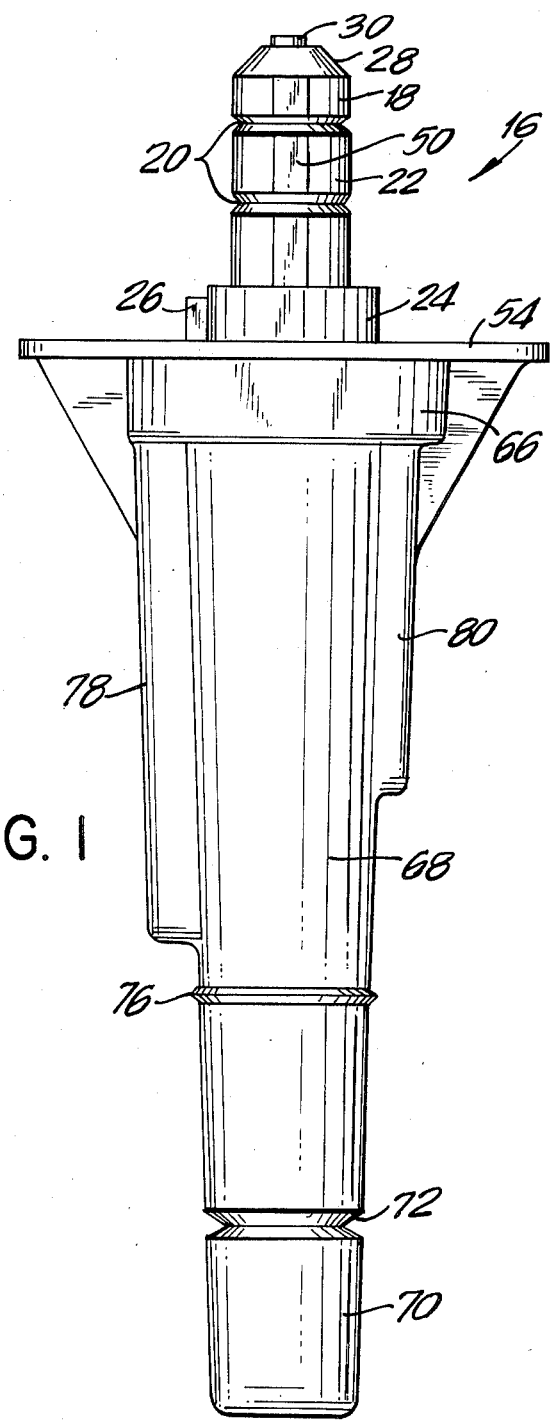
FIG. 1
FIG. 2

DENTAL PIN AND BUSHING ASSEMBLY

This invention relates to a dental pin and bushing assembly for coupling removable dies of prepared teeth to working casts.

BACKGROUND OF THE INVENTION

The use of working casts with removable dies has become very common in dental practice. Using any one of various known techniques, a cast can be produced from an impression in which the dies of the teeth being worked on are removably positioned. Typically, dowel pins are utilized to removably couple the dies to the cast. In most cases tapered dowel pins are utilized to facilitate insertion of the removable dies into the cast.

After the dies have been properly formed and indexed in the cast, one of the important aspects is to be able to return the dies back to their exact position in a repeatable manner in the cast. Additionally, the dies must remain stable when positioned in the cast, even when the cast is inverted.

One technique that is generally used for forming working casts with removable dies has been generally referred to as the "one-pour technique". In this technique, dowel pins are positioned over an impression tray and maintained suspended over the tray. Die stone is poured into the impression tray to form the full cast of the teeth and dies of the prepared-teeth to be worked on. After completion, the stems of the dowel pins project from the die. In another technique additional stone is poured to form the working cast with the dowel stems extending into and through the cast. This is known as a double pour technique. When the model stone or gypsum hardens the model is cut to separate the teeth and the stems are tapped to separate each section with the dowel pin from the cast base.

In such cases, the dowel pins with the attached die are reinserted directly into the cast stone base. The continuous reinsertion of the dowel pin dies into the die cast stone necessitated by the subsequent technical procedures, may cause crumbling of the stone, do not permit easy seating of the dowel pin, and often prevents the die from being repositioned properly in the cast base. Additionally, since there is only a dowel pin for reinsertion, even though it may be tapered, and keyed in some form or another, the problem of orientation of the die into the cast may not be sufficiently specific to that the die can be inserted in various indefinite and exact positions thereby making the fabrication of accurate dental restorations difficult.

In order to properly orient the placement of removable dies into the cast, there has been developed the PINDEX System by the Whaledent Company. Such system is described in U.S. Pat. No. 3,704,519. In such system, holes are formed into the removable part of the die. Pins with bushings are then inserted and the pins with the bushings are pressed downwardly into the material forming the cast. The cast material sets with the bushings in place whereupon the dies may be removed by extracting the pins from the bushings. By using the two pins, for each die section, proper replacement of the die section into the cast is ensured.

The need for proper orientation of each die section is thus seen to be an important aspect of using removable dies with working casts. Both in the one-pour technique as well as in the PINDEX technique, such orientation is significant and the ability to easily remove and replace the removable die is important.

SUMMARY OF THE INVENTION

Accordingly, it is an object of the present invention to provide a dental pin and bushing assembly for removable coupling of a die section of a tooth into a working cast.

Another object of the present invention provides a dental pin and bushing assembly which aides in the proper orientation of a removable die into a working cast.

Still a further object of the present invention is to provide a dental pin and bushing assembly which facilitates the use of the one-pour technique in making removable dies with working casts by aiding in the coupling of the die to the casts.

Yet another object of the present invention is to provide a dental pin and bushing assembly which can be utilized in the PINDEX technique of forming working casts and removable dies.

Yet another object of the present invention is to provide a dental pin and bushing assembly which provides means for securely retaining a pin within a removable die and a bushing within a working cast, and which facilitates insertion and removal of the die from the cast while retaining the die stable to prevent accidental falling out of the die.

Briefly, in accordance with the present invention, there is provided a dental pin and bushing assembly for removable coupling of a die of a tooth into a working cast. The assembly includes a pin which has an axially extending head portion which can be securely retained within the die. A coaxial body portion depends from the die. The body portion includes an offset for orienting the insertion of the pin in the bushing to be sure that it enters in only a single orientation. The bushing can be secured within the working cast and includes an elongated sleeve with an interior shape which matingly can receive the body portion of the pin.

In an embodiment of the invention, the pin is formed as a substantially cylindrical rod which includes at least one radially projecting rib extending along at least a portion of the length of the rod. Preferably, a pair of diametrically opposed ribs are included with one rib being larger than the other and extending longitudinally a greater length along the rod than the other.

The sleeve includes a shape which matingly receives the pin, including the cylindrical rod and the opposing ribs. The sleeve also includes a distal end which can be snipped off to expose the tip of the rod.

In use, the head of the pin is inserted into the removable die. The cylindrical rod and projecting ribs depend from the die. The sleeve is secured within the cast. The distal end of the sleeve is removed to expose the end of the rod therethrough thereby permitting pushing up on the end of the rod to remove the die section from the cast.

The bushing can include a flat flange at the upper end of the sleeve serving as a platform at the top of the cast for receiving the base surface of the removable die section.

The aforementioned objects, features and advantages of the invention will, in part, be pointed out with particularity, and will, in part, become obvious from the following more detailed description of the invention, taken in conjunction with the accompanying drawing, which form an integral part thereof.

BRIEF DESCRIPTION OF THE DRAWING

In the drawing:

FIG. 1 is an exploded perspective view of the dental pin and bushing assembly in accordance with the present invention in an unassembled condition;

FIG. 2 is an elevational view of the dental pin and bushing assembly in the assembled condition;

In the various figures of the drawing, like reference characters designate like parts.

DESCRIPTION OF THE PREFERRED EMBODIMENT

Figure 3:
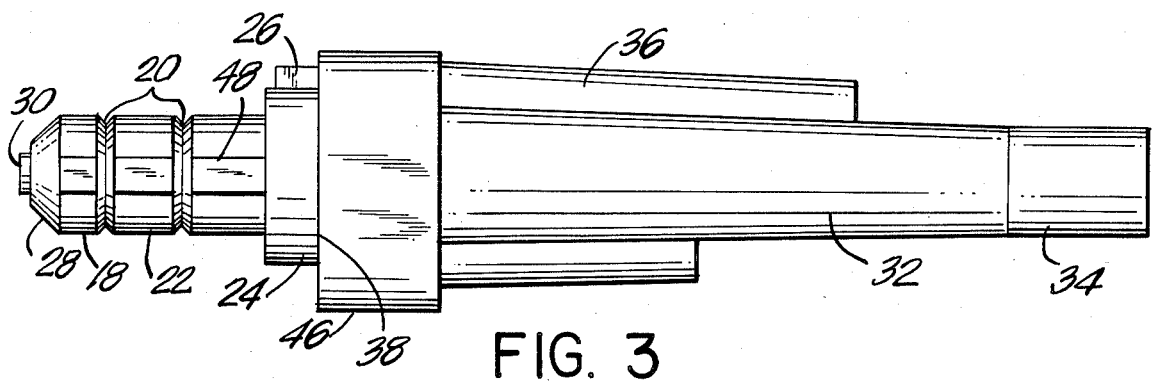
FIG. 3 is an elevational view of the dental pin.
Figure 4:
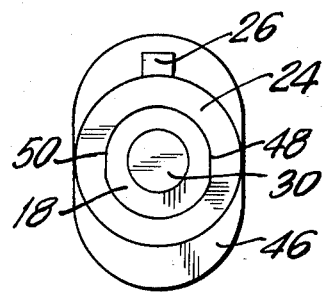
FIG. 4 is a top end view thereof.
Figure 5:
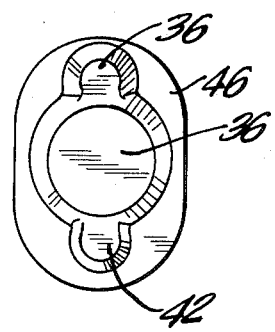
FIG. 5 is a bottom end view thereof.
Figure 6:
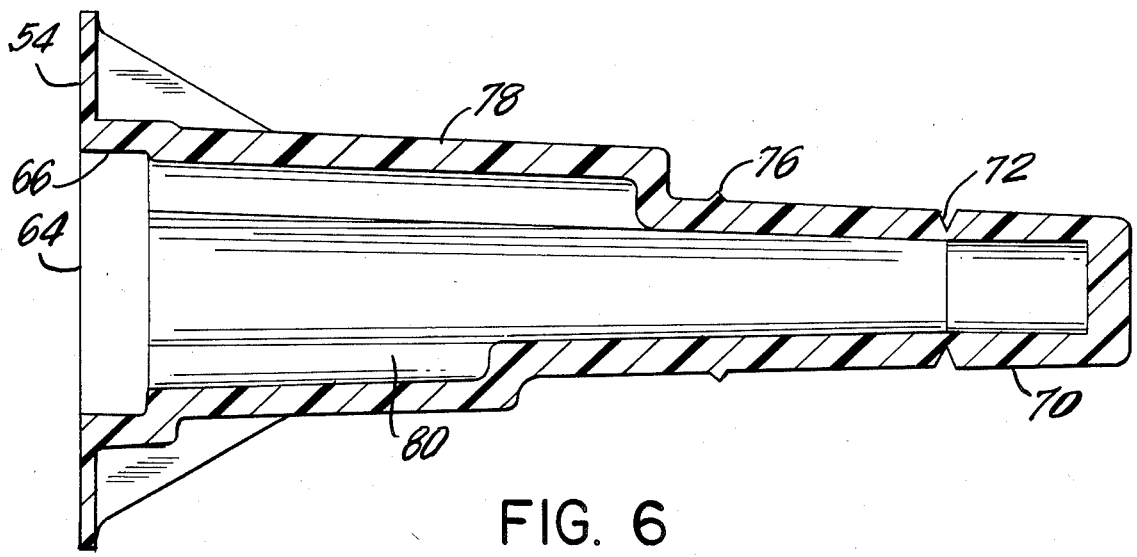
FIG. 6 is a cross sectional view taken longitudinally through the center of the bushing.
Figure 7:
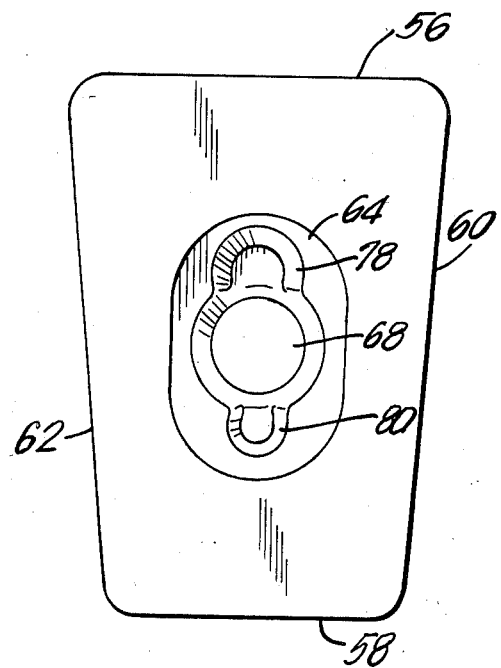
FIG. 7 is a top end view thereof.
Figure 8:
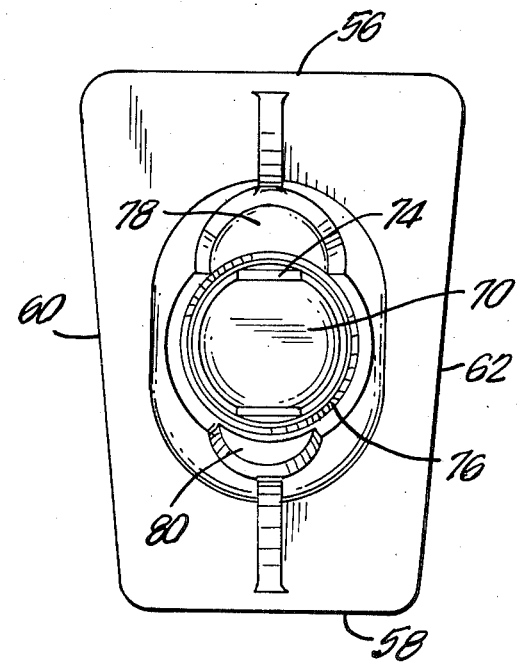
FIG. 8 is a bottom end view thereof.

Referring now to FIGS. 1-8, there is shown the assembly of the present invention, shown generally at 10 including a dental pin, shown generally at 12 for insertion within a bushing shown generally at 14. The dental pin includes a substantially cylindrical head portion 16 and an elongated, substantially cylindrical body portion 18. The head portion includes a cylindrical stem 19 with a plurality of annular grooves 20 at spaced apart locations leaving raised portions 22 therebetween. At the bottom of the head portion 16 there is provided an annular collar 24 of substantially circular configuration. A projecting key 26 extends from the collar 24. At its upper end, the head portion is shaped in a conical end 28 terminating in an upper cap 30.

The body portion 18 includes an elongated substantially cylindrical rod 32 which is slightly tapered in a downward direction but terminates in a cylindrical, untapered distal end 34. Positioned on one side is a radially projecting rib 36 extending along the length of the rod 32 commencing from an upper edge and terminating at a lower end 40. As can best be seen in FIG. 5, rib 36 has a substantially circular cross sectional configuration and is positioned tangentially with respect to the rod 32.

Diametrically opposed to the rib 36, is a similar rib 42. Rib 42 likewise commences at an upper end 38 and terminates at a lower end 44 extending along the length of the rod 32. As can best be seen in FIG. 5, rib 42 likewise has a circular cross sectional configuration and also is positioned tangentially with respect to rod 32. The diameter of the rib 36 is noted to be larger than the diameter of the rib 42.

At the upper end of the body portion, and spaced between the head portion is an enlarged substantially rectangular collar 46 having rounded corners. It should also be noted, as can best be seen in FIG. 4, that the head portion has a pair of opposing flats 48, 50 in either side thereof.

The bushing 14 comprises a lower sleeve portion 52 and an upper flange 54. The flange is substantially planar and includes a trapezoidal configuration as can best be seen in FIG. 7 having a wide edge 56, a narrow edge 58, and interconnecting angled edges 60, 62. The flange is supported by optional struts 57. An aperture 64 is formed into the flange 54 having a configuration corresponding to the substantially rectangular collar 46 on the pin section. The aperture 64 leads to an internal cavity 66 continuing with the same configuration to accommodate the collar 46 in countersunk fashion.

The sleeve portion 52 includes substantially cylindrical center tube 68 which is downwardly tapered along its entire length until it reaches the lower distal tip portion 70. The tip portion 70 is cylindrical and untapered. A reduced diameter throat 72 separates the distal tip from the main part of the tube 68 to permit snipping off or removal of the tip 70. As can best be seen in FIG. 8, the lower tip 70 can include a pair of flats 74, 76 to permit grasping by a tool in order to facilitate removal of the lower tip 70.

Spaced along the length of the tubular portion 68 are projecting dimples 76 which serve to facilitate retention of the sleeve in a working cast, as will hereinafter be explained.

Positioned along one side of the tube 68 is a receiving chamber 78 which projects radially outward and extends along a length of the tube 68. Diametrically opposed thereto is another radially projecting chamber 80 likewise extending along a length of the tube 68. As can best be seen in FIG. 7, the cross sectional diameter of the chamber 78 is substantially circular as is the cross sectional shape of the chamber 80. The diameter of chamber 78, however, is larger than that of 80. The two chambers 78, 80, merge with the interior space within the tube 68 to form one large space to receive the body portion of the pin heretofore described. The length of the chamber 78 extends longer than that of the chamber 80.

Both the chambers 78 and 80 are downwardly tapered as are the ribs 36, 42 of the dental pin. Accordingly, as can best be seen in FIG. 2, the pin snugly fits within the bushing to form a composite assembly.

The heretofore described dental pin and bushing assembly of the present invention finds use in connection with the formation of removable dies with dental casts in a dental model. By way of example, its use will be described in connection with the one-pour technique. In such technique, a dental impression is first made including the prepared teeth which are being worked on. The dental pin and bushing assembly of the present invention is then positioned over each prepared tooth in the impression. The pins are positioned with the head portions facing downwardly into the impression and the assembled bushing projecting upwardly. The pins and bushing assembly can be held in place by any of the well known means, such as common bobby pins and straight pins retaining the pins and bushing assembly in a vertically oriented position.

Die stone is then poured into the impression covering the pins and the bushings. After the die has set a saw is used to cut through on either side of the tooth being worked on until the flange of the bushing is reached. The tip of the bushing having been snipped off, the end of the pin is available for tapping. The die section of the tooth will then loosen to remove the die tooth from its base.

The present invention can also be used in a double-pour technique. In such technique die stone is first poured into the impression filling the impressions of the teeth and covering the head portion of the pins until the flange of the bushing is reached. It should be appreciated, that the presence of the flange provides a visual indicator of the amount of die stone to be inserted into the impression tray. As is well known, paper clips, look washers or other similar items are placed in the stone before it sets in those sections not including the prepared teeth. These retentive devices will aid in retaining the cast which will be later placed.

In placing the dental pin and bushing assembly of the present invention into the impression tray, the flange which is trapezoidal in shape, aids in its proper placement. The wide edge of the flange is placed adjacent the distal side of the impression while the narrow edge of the flange is placed on the mesial side. This corresponds to the arch of the mouth with the wider arch being at the distal side. It should also be noted, that the longer rib is on the same side as the wider edge of the flange so that the longer rib will be provided at the distal edge. A single dental pin and bushing assembly is all that is required for each die section since the dental pin and bushing assembly of the present invention provides proper orientation for reassembly, as will hereinafter be described.

After the die stone has set, the straight pins, bobby pins, and other portions are removed from the impression. The die stone is lubricated in order to permit easier separation of the dies from the working cast after the working cast is formed. Typically, wax will be placed on the end of the bushing. The stone is then poured to form the base portion of the cast. After the stone is set the wax is removed and the distal ends of the bushing is uncovered, and if necessary by forming a channel in the bottom of the base portion of the cast. The tip of the bushing is then snipped off and removed by either application of a tool or other means.

The undercut throat 72 facilitates removal of the tip. The cylindrical, untapered distal portion of the pin projects through the end of the sleeve. It should be appreciated that the end 70 can be provided as a separate cap member which is removed after the bushing is seated in the cast base. Removal of the cap exposes the distal end of the pin.

A saw is used to cut through the layer of die stone on either side of the die sections to be removed. The projecting end of the pin is then tapped gently in order to loosen the die from the cast. The portions are then trimmed.

The present dental pin and bushing assembly would also find use in connection with PINDEX method. In such method, a hole would be drilled into the die section and the head portion of the present dental pin and bushing assembly inserted therein. The bushing would then be mounted into the not yet hardened portion of the base and the bushing permitted to harden. The die portion would then be removable from the base portion. Only one such dental pin and bushing assembly of the present invention is required to be inserted, although heretofore, in the PINDEX system, as least two such pins were required in order to require proper orientation.

Figure 9:
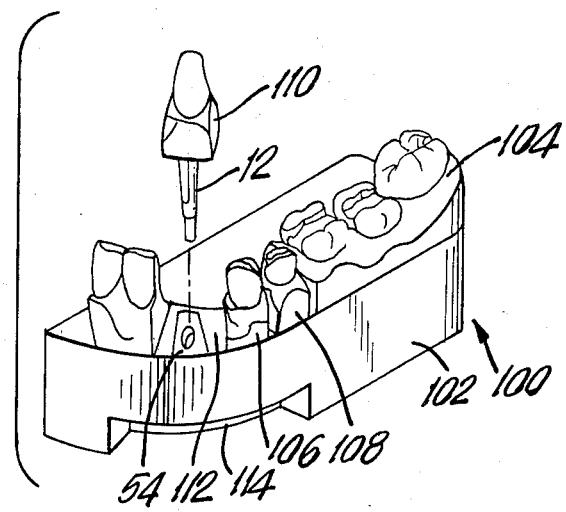
FIG. 9 is a perspective view of a working cast showing a removable die section utilizing the dental pin and bushing assembly, with the removable die shown extracted from the working cast.

The benefits of the present dental pin and bushing assembly can best be seen by reference to FIG. 9. In FIG. 9, there is generally shown a working cast 100 with the base portion 102 and the upper die portion 104. The particular prepared teeth have been sectioned off and includes the removable portions 106, 108 and 110 with the portion 110 shown in its removed state from the cast.

The upper flange 54 of the bushing can be seen projecting above the upper surface 112 of the base 102. Likewise, the body portion 12 of the pin is seen depending from the removable die section 110. It should be noted, that the upper flange 54 serves as a platform for receiving the removable die section 110. Its wide edge faces forward at the distal end and its narrow edge faces the mesial edge of the teeth conforming to the arch shape.

Because the ribs have different lengths and different diameters, the removable die section can only fit into the bushing in a single orientation. If one were to try to reverse the die section, or put it in any other way, it would be blocked and it would not seat into the bushing. The presence of the ribs provides directivity permitting orientation in only a single way. As a result, the die section can only be reinserted in its original position even though there is only a single dental pin and bushing assembly present.

Figure 10:
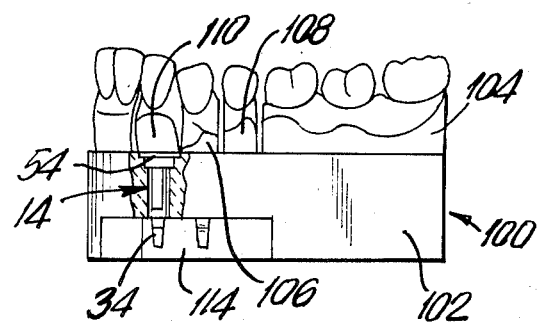
FIG. 10 is an elevational view of FIG. 9 showing the die reinserted in the cast with the cast partially broken away to show the use of the dental pin and bushing assembly.

It should also be appreciated, that because of the tapered structure of the pin and the corresponding tapered sleeve, the die section will fit snugly as it is pushed into place so that even though the cast is inverted or shaken the die sections will not automatically fall out. In fact, as is shown in FIG. 10, the lower cylindrical end 34 of the pin projects into the notch 114 provided in the base 102 of the working cast 100. Pushing up on the distal end 34 facilitates release of the die section 110.

The presence of the keyway 26 in the collar 24 of the head of the pin aides in securing the head within the die section and preventing rotation in the die section. The presence of the dimples 76 on the sleeve as well as the side ribs and the corresponding sleeves likewise aid in retention and prevent rotation of the parts within their corresponding cast portions.

It should be noted, that by having one rib short and one rib long, a number of benefits are obtained. Firstly, it prevents insertion in the wrong direction since the long rib would hit the bottom of the short rib sleeve chamber and would not be fully inserted. Additionally, as is best noted in FIG. 1, because of the short and long ribs, there is provided a counterbalance along line 120, as shown in dotted lines, since the two ends are not on the same plane. This aids in the distribution of forces both on the pin as well as on the sleeve.

Typically, the sleeve will be made out of plastic material, however it could also be made out of aluminum or zinc. The pin would typically be made out of zinc.

There has been disclosed heretofore the best embodiment of the invention presently contemplated. However, it is to be understood that various changes and modifications ma be made thereto without departing from the spirit of the invention.

I claim:

1. A dental pin and bushing assembly for removable coupling of a die of a tooth into a working cast comprising:

a pin having an axially extending head portion for secured retention within the die, a coaxial body portion for depending projection from the die portion, the body portion include offset means for oriented insertion of the pin; and a bushing for securement within the working cast having an elongated sleeve with an interior shape for matingly receiving the body portion of the pin, and wherein the body portion of the comprises a substantially cylindrical rod and a first radially projecting rib extending along at least a portion of the length of the rod, and further comprising a second radially projecting rib extending along at least a portion of the length of rod in diametric opposition to the first rib.

2. A dental pin and bushing assembly as in claim 1, wherein one of said ribs extends along a greater length of the rod than the other rib.

3. A dental pin and bushing assembly as in claim 2, wherein both ribs commence from a top of said body portion.

4. A dental pin and bushing assembly as in claim 3, and further comprising an enlarged collar at the top of the body portion.

5. A dental pin and bushing assembly as in claim 1, wherein both said ribs are substantially circular in cross section and positioned tangentially with respect to said rod.

6. A dental pin and bushing assembly as in claim 5, wherein the diameter of one rib is larger than the diameter of the other rib.

7. A dental pin and bushing assembly as in claim 5, wherein said rod and said ribs are downwardly tapered.

8. A dental pin and bushing assembly as in claim 7, wherein said rod comprises a cylindrical untapered foot at its distal end.

9. A dental pin and bushing assembly as in claim 1, wherein said head portion comprises a substantially cylindrical stem having grooves thereon for aiding in the retention of the pin.

10. A dental pin and bushing assembly as in claim 9, and further comprising an enlarged annular collar at the base of the head portion.

11. A dental pin and bushing assembly as in claim 10, and further comprising key means radially projecting from said enlarged collar for aiding in the retention of the pin.

12. A dental pin and bushing assembly for removable coupling of a die of a tooth into a working cast comprising:
- a pin having an axially extending head portion for secured retention within the die, a coaxial body portion for depending projection from the die portion, the body portion include offset means for oriented insertion of the pin; and
- a bushing for securement within the working cast having an elongated sleeve with an interior shape for matingly receiving the body portion of the pin, and
- wherein said bushing further comprises an enlarged flange at an upper end of the sleeve providing a platform at a top of the working cast, and
- wherein said flange has a trapezoidal planar configuration including a wide edge and a narrow edge, the wide edge for positioning adjacent to the distal side of the cast and the narrow edge along the mesial side of the cast to conform to the arch shape of the mouth.

13. A dental pin and bushing assembly for removable coupling of a die of a tooth into a working cast comprising:
- a pin having an axially extending head portion for secured retention within the die, a coaxial body portion for depending projection from the die portion, the body portion include offset means for oriented insertion of the pin; and
- a bushing for securement within the working cast having an elongated sleeve with an interior shape for matingly receiving the body portion of the pin, and
- wherein the sleeve comprises a central substantially cylindrical tube portion, and at least one radially projecting chamber longitudinally extending along at least a part of the tube portion, and
- comprising a further radially projecting chamber longitudinally extending along at least a part of the tube portion, said chambers being in diametric opposition to each other and one chamber extending along a greater length of the tube portion than the other chamber.

14. A dental pin and bushing assembly as in claim 13, and further comprising a flange at an upper end of the sleeve having a trapezoidal planar configuration including a wide edge and a narrow edge, the wide edge being on the same side of the tube portion as the longer extending chamber and the narrow edge being on the same side of the tube portion as the shorter extending chamber.

15. A dental pin and bushing assembly as in claim 13, wherein said tube portion and said chambers are downwardly tapered.

16. A dental pin and bushing assembly as in claim 13, wherein said chambers are substantially circular in cross sectional configuration.

17. A dental pin and bushing assembly as in claim 16, wherein the diameter of one chamber is larger than the diameter of the other chamber.

18. A dental pin and bushing assembly for removable coupling of a die of a tooth into a working cast comprising:
- a pin having an axially extending head portion for secured retention within the die, a coaxial body portion for depending projection form the die portion, the body portion include offset means for oriented insertion of the pin; and
- a bushing for securement within the working cast having an elongated sleeve with an interior shape for matingly receiving the body portion of the pin, and
- wherein said bushing further comprises an upper end of the sleeve for positioning at a top of the working cast, and
- further comprising a countersunk cavity beneath said upper end for receiving an annular collar on the pin.

19. A dental pin and bushing assembly for removable coupling a of a die of a tooth into a working cast comprising:
- a pin having an axially extending head portion for secured retention within the die, a coaxial body portion for depending projection from the die portion, the body portion include offset means for oriented insertion of the pin; and
- a bushing for securement within the working cast having an elongated sleeve with an interior shape for matingly receiving the body portion of the pin, and
- a dental pin and bushing assembly wherein said sleeve includes a substantially cylindrical portion and comprising an annular reduced diameter throat portion adjacent a distal end of the cylindrical portion for removal of the distal end.

20. A dental pin and bushing assembly as in claim 19, wherein the cylindrical portion is downwardly tapered and wherein said distal end is untapered.

21. A dental pin and bushing assembly as in claim 19, wherein said distal end includes opposing flats to facilitate grabbing for removal.

* * * * *